(12) United States Patent  
Stefan

(10) Patent No.: US 11,871,956 B2  
(45) Date of Patent: Jan. 16, 2024

(54) MEDICAL SCISSORS FOR MICROINVASIVE APPLICATIONS

(71) Applicant: KARL STORZ SE & Co. KG, Tuttlingen (DE)

(72) Inventor: Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 154 days.

(21) Appl. No.: 17/119,201

(22) Filed: Dec. 11, 2020

(65) Prior Publication Data

US 2021/0177449 A1 Jun. 17, 2021

(30) Foreign Application Priority Data

Dec. 11, 2019 (DE) ...................... 10 2019 134 017.9

(51) Int. Cl.
*A61B 17/3201* (2006.01)
*A61B 17/29* (2006.01)

(52) U.S. Cl.
CPC .......... *A61B 17/3201* (2013.01); *A61B 17/29* (2013.01); *A61B 2017/2933* (2013.01); *A61B 2017/2945* (2013.01); *A61B 2017/2947* (2013.01)

(58) Field of Classification Search
CPC . A61B 17/3201; A61B 18/085; A61B 18/146; A61B 17/295; A61B 17/320052
See application file for complete search history.

(56) References Cited

U.S. PATENT DOCUMENTS

| 4,938,215 A | * | 7/1990 | Schulman | ............ | A61B 17/122 |
| | | | | | 606/174 |
| 2005/0222598 A1 | * | 10/2005 | Ho | ...................... | A61B 17/3201 |
| | | | | | 606/171 |
| 2008/0287926 A1 | * | 11/2008 | Abou El Kheir | .. | A61B 17/3421 |
| | | | | | 606/1 |
| 2010/0298852 A1 | * | 11/2010 | Slater | ............. | A61B 17/320016 |
| | | | | | 606/205 |

(Continued)

FOREIGN PATENT DOCUMENTS

| CN | 111557708 A | * | 8/2020 | ..... A61B 17/320016 |
| DE | 202018102182 U1 | | 7/2019 | |

(Continued)

*Primary Examiner* — Timothy J Neal  
*Assistant Examiner* — James R McGinnity  
(74) *Attorney, Agent, or Firm* — McGlew and Tuttle, P.C.

(57) ABSTRACT

Microinvasive medical scissors include a first scissor blade (30) with a first cutting edge (35, 36) between a flank surface (33) and a beveled surface (37, 38), a relatively moveable second scissor blade (40) with a second cutting edge (45, 46) between a flank surface (43) and a beveled surface (47, 48), a guiding device (24) for mechanical guiding of the second cutting edge to touch the first cutting edge at any time in a point of intersection (50). The guiding device is connectable to a shaft (16) of a microinvasive instrument (10). The cutting edges have respective parameters which increase and decrease several times along the second cutting edge. The parameters are the wedge angle ($\beta_1$, $\beta_2$,) between the flank surface and the beveled surface, the cutting angle ($\delta_1$, $\delta_2$), or the width (b1, b2) of the beveled surface.

19 Claims, 3 Drawing Sheets

(56) References Cited

U.S. PATENT DOCUMENTS

2013/0046323 A1* 2/2013 Whitaker ........... A61B 17/3201
606/174
2014/0228871 A1* 8/2014 Cohen .............. A61B 17/32053
606/170

FOREIGN PATENT DOCUMENTS

| EP | 3213702 A1 | 9/2017 |
| JP | 2013138844 A | 7/2013 |
| WO | 2019050025 A1 | 3/2019 |

* cited by examiner

MEDICAL SCISSORS FOR MICROINVASIVE APPLICATIONS

CROSS REFERENCE TO RELATED APPLICATIONS

This application claims the benefit of priority under 35 U.S.C. § 119 of German Application 10 2019 134 017.9, filed Dec. 11, 2019, the entire contents of which are incorporated herein by reference.

TECHNICAL FIELD

The present invention pertains to medical scissors for microinvasive applications and to a medical instrument with such scissors.

TECHNICAL BACKGROUND

Medical scissors for microinvasive applications must meet special and especially high requirements. These requirements arise, on the one hand, from the small dimensions which per se already make difficult or rule out a transfer of concepts that have been tried and tested in markedly larger scissors. In addition, on the other hand, requirements for a special reliability, which result from the special application situation. In view of markedly less direct mechanical control and markedly less direct mechanical feedback, medical scissors for microinvasive applications shall cut reliably at the time of each closing. A clamping of the material to be cut between the scissor blades instead of a cutting or a slipping away of the material to be cut distally may not only prolong the duration of a microinvasive action, but may put the health of the patient at risk in individual cases.

SUMMARY

An object of the present invention is to create improved medical scissors for microinvasive applications and an improved medical instrument having such scissors.

Embodiments of the present invention are based on the idea of configuring the properties of the cutting edges of the scissor blades, especially the wedge angle or the cutting angle or the widths of the beveled surface in an oscillating manner, i.e., alternately increasing several times and decreasing several times.

Medical scissors for microinvasive applications comprises a first scissor blade with a first cutting edge between a flank surface and a beveled surface, a second scissor blade, which is movable in relation to the first scissor blade, with a second cutting edge between a flank surface and a beveled surface and a guiding device for the mechanical guiding of the second scissor blade in relation to the first scissor blade such that the second cutting edge touches the first cutting edge at any time in a point of intersection, wherein the guiding device is connected or can be connected rigidly to a shaft of a microinvasive instrument, wherein the first cutting edge is characterized by a first parameter, which increases several times and decreases several times along the first cutting edge, wherein the second cutting edge is characterized by a second parameter, which increases several times and decreases several times along the second cutting edge, wherein the first parameter and the second parameter are in each case the wedge angle between the flank surface and the beveled surface or the cutting angle or the width of the beveled surface.

The cutting edges are convex, sharp edges, which are also designated as facets of a blade in the case of scissors. The cutting angle is the sum of the clearance angle and the wedge angle. The beveled surface is the plane or slightly curved surface directly adjacent to the cutting edge.

The guiding device and the cutting edges are especially configured and arranged such that the cutting edges touch one another at any time in precisely one point of intersection.

The guiding device is, for example, a joint, which exclusively makes possible in a positive-locking manner a pivoting of the second scissor blade in relation to the first scissor blade about a pivot axis defined in a positive-locking manner by the joint. The joint can make possible a pivoting of both scissor blades about a common pivot axis or about two different pivot axes in relation to the distal end of the shaft. As an alternative, the first scissor blade may be connectable or can be connected rigidly, i.e., immovably to the distal end of a shaft.

The guiding device is connected or can be connected mechanically to the distal end of the shaft in an especially non-destructive, detachable manner. As an alternative, the guiding device may be connected permanently and not in a non-destructive, detachable manner to the distal end of the shaft.

The first parameter increases at least twice and decreases twice especially alternately along the first cutting edge. The second parameter decreases at least twice and increases twice especially alternately along the second cutting edge. The first parameter and the second parameter may each vary along the cutting edges continuously or intermittently, i.e., in increments. The first parameter and the second parameter may each oscillate between a predefined minimum and a predefined maximum and with a constant spatial period. As an alternative, the variations of the first parameter and of the second parameter may vary both in the period and in the amplitude, i.e., the difference of adjacent minima and maxima. The location dependency and the rates of change of the parameters may also repeat or not repeat along the cutting edges.

The same parameters or different parameters may vary at the first cutting edge and at the second cutting edge. For example, the wedge angle may vary at both cutting edges or the cutting angle may vary at both cutting edges or the widths of the beveled surfaces may vary at both cutting edges. As an alternative, for example, the wedge angle may vary at one cutting edge and the width of the beveled surface may vary at the other cutting edge.

In medical scissors, as they are described here, especially the first cutting edge has a first section, in which the first parameter is not greater than a first predefined value, and a second section, in which the first parameter is not smaller than a second predefined value, which is greater than the first predefined value, wherein the second cutting edge has a first section, in which the second parameter is not greater than a third predefined value, and a second section, in which the second parameter is not smaller than a fourth predefined value, which is greater than the third predefined value, wherein the second section of the first cutting edge is located opposite the first section of the second cutting edge and the second section of the second cutting edge is located opposite the first section of the first cutting edge.

In medical scissors, as they are described here, especially the first cutting edge has alternately first sections in which the first parameter is not greater than a first predefined value and second sections, in which the first parameter is not smaller than a second predefined value, which is greater than the first predefined value, wherein the second cutting edge has first sections, in which the second parameter is not greater than a third predefined value, and second sections, in which the second parameter is not smaller than a fourth predefined value, which is greater than the third predefined value.

In medical scissors, as they are described here, especially the first cutting edge has alternately first sections in which the first parameter is not greater than a first predefined value and second sections, in which the first parameter is not smaller than a second predefined value, which is greater than the first predefined value, wherein the second cutting edge has alternately first sections, in which the second parameter is not greater than a third predefined value, and second sections, in which the second parameter is not smaller than a fourth predefined value, which is greater than the third predefined value, wherein each second section of the first cutting edge is located opposite a first section of the second cutting edge and each second section of the second cutting edge is located opposite a first section of the first cutting edge.

The first predefined value is especially the smallest value, which the first parameter has along the entire first cutting edge. As an alternative, the first parameter may attain a value that is smaller than the first predefined value within the first section or within the first sections of the first cutting edge and, as an alternative or in addition, outside of the first section or outside of the first sections. The second predefined value is especially the largest value, which the first parameter attains along the entire first cutting edge. As an alternative, the second parameter may attain a value that is greater than the second predefined value within the second section or within the second sections of the first cutting edge and, as an alternative or in addition, outside of the second section or outside of the second sections of the first cutting edge.

The third predefined value is especially the smallest value which the second parameter attains along the entire second cutting edge. As an alternative, the second parameter may attain a value, which is smaller than the third predefined value within the first section or within the first sections of the second cutting edge and, as an alternative or in addition, outside of the first section or outside of the first sections of the second cutting edge. The fourth predefined value is especially the largest value, which the second parameter attains along the entire second cutting edge. As an alternative, the second parameter within the second section or within the second sections of the second cutting edge and, as an alternative or in addition, outside of the second section or outside of the second sections of the section cutting edge may attain a value that is greater than the fourth predefined value.

In medical scissors, as they are described here, especially the first cutting edge has alternately first sections, in which the first parameter is smaller than a first predefined value, and second sections, in which the first parameter is greater than the first predefined value, wherein the second cutting edge has alternately first sections, in which the second parameter is smaller than a third predefined value, and second sections, in which the second parameter is greater than the third predefined value, wherein each second section of the first cutting edge is located opposite a first section of the second cutting edge and each second section of the second cutting edge is located opposite a first section of the first cutting edge.

Directly adjacent first and second sections of the first cutting edge may be directly adjacent to one another or separated by areas (which are point-like in the mathematical sense), in which the first parameter is neither smaller nor greater than, but rather is identical to the first predefined value. The same applies to the first and second sections of the second cutting edge.

The first cutting edge has especially two, three, four or more first sections and two, three, four or more second sections. The second cutting edge has especially two, three, four or more first sections and two, three, four or more second sections.

A point at the first cutting edge corresponds to a point at the second cutting edge, when there is a configuration of medical scissors, in which the point at the first cutting edge and the point at the second cutting edge are at the same time identical to the point of intersection of the cutting edges. A section of the first cutting edge is located opposite a section of the second cutting edge, when points within the section of the first cutting edge corresponding to points within the section of the second cutting edge form at least half or at least two thirds or at least three fourths of the section of the first cutting edge and at the same time points within the section of the second cutting edge corresponding to points within the section of the first cutting edge form a corresponding percentage of the section of the second cutting edge.

Because of the smaller wedge angle and/or because of the smaller cutting angle and/or because of the smaller width of the beveled surface, first sections of the first cutting edge and first sections of the second cutting edge cut more readily or better than second sections of the first cutting edge and second sections of the second cutting edge. By a first section of the second cutting edge being located opposite each second section of the first cutting edge and a first section of the first cutting edge being located opposite each second section of the second cutting edge, the medical scissors have at least either well-cutting first sections of the first cutting edge or well-cutting first sections of the second cutting edge especially continuously or with small gaps along the cutting edges. At the same time, the profiling of the cutting edges by the alternating arrangement of first sections and of second sections prevent or at least reduce the risk of a slipping away of a material to be cut distally.

In medical scissors, as they are described here, the first sections and the second sections of the first cutting edge and the first sections and the second sections of the second cutting edge are especially arranged such that the point of intersection is located at any time at least either at a first section of the first cutting edge or at a first section of the second cutting edge during the closing of the medical scissors.

This may make possible a continuous, good cutting action of the medical scissors.

In medical scissors, as they are described here, the first sections and the second sections of the first cutting edge and the first sections and the second sections of the second cutting edge are especially arranged such that during the closing of the medical scissors areas, in which the point of intersection is located neither at a first section of the first cutting edge nor at a first section of the second cutting edge, are not larger than adjacent areas, in which the point of intersection is located at a first section of the first cutting edge or at a first section of the second cutting edge.

Especially areas of the angle between the scissor blades or areas of the coordinates of the point of interaction along one of the two cutting edges are meant by areas.

The especially good cutting property is only interrupted briefly by the short interruptions between areas, in which the point of intersection is located either at a first section of the first cutting edge or at a first section of the second cutting edge.

In medical scissors, as they are described here, the first parameter is identical to the first predefined value especially at least either in each first section of the first cutting edge or the second parameter is identical to the third predefined value in each first section of the second cutting edge.

In other words, the first parameter is constant, namely especially minimal within the first sections of the first cutting edge, and the second parameter is constant, namely especially minimal within the first sections of the second cutting edge.

In medical scissors, as they are described here, the first predefined value and the third predefined value are especially identical.

In medical scissors, as they are described here, the first parameter is identical to the second predefined value especially at least either in each second section of the first cutting edge or the second parameter is identical to the fourth predefined value in each second section of the second cutting edge.

In other words, the first parameter is constant, namely especially maximal within the second sections of the first cutting edge, and the second parameter is constant, namely especially maximal within the second sections of the second cutting edge.

In medical scissors, as they are described here, the second predefined value and the fourth predefined value are especially identical.

In medical scissors, as they are described here, the wedge angle of the first cutting edge is not greater than 20° or not greater than 30° or not greater than 40° especially in each first section of the first cutting edge, wherein the wedge angle of the second cutting edge is not greater than 20° or not greater than 30° or not greater than 40° in each first section of the second cutting edge.

In medical scissors, as they are described here, the wedge angle of the first cutting edge is not smaller than 60° or not smaller than 70° or not smaller than 80° especially in each second section of the first cutting edge, wherein the wedge angle of the second cutting edge is not smaller than 60° or not smaller than 70° or not smaller than 80° in each second section of the second cutting edge.

In medical scissors, as they are described here, the width of the beveled surface of the first cutting edge is not greater than a 20th or not greater than a 50th or not greater than a 100th of the length of the first cutting edge especially in each first section of the first cutting edge, wherein the width of the beveled surface of the second cutting edge is not greater than a 20th or not greater than a 50th or not greater than a 100th of the length of the second cutting edge in each first section of the second cutting edge.

In medical scissors, as they are described here, the width of the beveled surface at the first cutting edge is not smaller than a 20th or smaller than a 10th of the length of the first cutting edge especially in each second section of the first cutting edge, wherein the width of the beveled surface of the second cutting edge is not smaller than a 20th or not smaller than a 10th of the length of the second cutting edge in each second section of the second cutting edge.

In medical scissors, as they are described here, a side of the first scissor blade facing away from the flank surface has grooves that are oriented essentially at right angles to the first cutting edge, wherein the first sections of the first cutting edge are each present in a groove, wherein the second sections of the first cutting edge are each present between adjacent grooves.

A groove is essentially at right angles to a cutting edge, when the groove forms with the cutting edge an angle of at least 60° or of at least 70° or of at least 80°. Each groove may have a depth that is constant or constant at least over one section or is essentially constant. As an alternative, each groove may have a varying depth, especially a depth which at first increases within a comparatively short section away from the cutting edge and then decreases within a comparatively long section. Each groove may be linear or curved and have a constant or a varying cross section.

In particular, the cross sections of all grooves on the side of the first scissor blade facing away from the flank surface have identical or similar cross sections. The cross sections of the grooves on the side of the first scissor blade facing away from the flank surface may vary uniformly from groove to groove along the scissor blade.

Grooves on a side of the scissor blade facing away from the flank surface may, on the one hand, be able to be produced in an especially simple manner and effectively spatially modulate the property of the cutting edge of the scissor blade, on the other hand.

In medical scissors, as they are described here, the cross section of a groove especially has a linear edge section that is parallel to the first cutting edge.

In particular, at the first cutting edge, the linear edge section of the cross section of the groove passes over into the first cutting edge.

In medical scissors, as they are described here, a web which remains between adjacent grooves has especially a rounded cross section.

A rounded cross section has especially radii of curvature, which are not smaller than one third or not smaller than one fourth of the linear dimensions of the cross section.

In medical scissors, as they are described here, a side of the second scissor blade facing away from the flank surface has grooves that are oriented essentially at right angles to the second cutting edge, wherein the first sections of the second cutting edge are each present in a groove, and wherein the second sections of the second cutting edge are each present between adjacent grooves.

In medical scissors, as they are described here, the cross section of a groove has especially a linear edge section that is parallel to the second cutting edge.

In medical scissors, as they are described here, a web which remains between adjacent grooves has especially an angular cross section.

An angle or, as an alternative, a plurality of angles of the cross section of the web between adjacent grooves and one or more corresponding convex edges of the web may prevent or hinder a sliding of tissue along the cutting edge in a positive-locking manner.

In medical scissors, as they are described here, a side of the first scissor blade facing away from the flank surface has especially a plurality of first surface areas, which are partial areas of a first flat or slightly curved surface, and a plurality of second surface areas, which are partial areas of a second flat or slightly curved surface, wherein each first section of the first cutting edge is present in a first surface area of the first scissor blade and each second section of the first cutting edge is present in a second surface area of the first scissor blade.

The side of the first scissor blade facing away from the flank surface adjoins the flank surface of the first scissor blade in the first cutting edge. When the first surface areas are partial areas of a first slightly curved surface, the radii of curvature of the first slightly curved surface are continuously greater than or much greater than the length of the first scissor blade. When the second surface areas are located in a second slightly curved surface, the radii of curvature of the second slightly curved surface are especially greater than or much greater than the length of the first scissor blade.

The first surface areas of the first scissor blade are especially first partial areas of the beveled surface of the first scissor blade, in which the wedge angle or the cutting angle is relatively small. The second surface areas of the first scissor blade are especially second partial areas of the beveled surface of the first scissor blade, in which the wedge angle or the cutting angle is relatively large.

In medical scissors, as they are described here, the flank surface, the first flat or slightly curved surface, in which the first surface areas of the first scissor blade are located, and the second flat or slightly curved surface, in which the second surface areas of the first scissor blade are located, intersect one another in the first cutting edge.

The first sections of the first cutting edge are areas of the cutting edge, in which the first surface areas adjoin the flank surface, and the second sections of the first cutting edge are areas, in which the second surface areas adjoin the flank surface.

In medical scissors, as they are described here, a side of the second scissor blade facing away from the flank surface has especially a plurality of first surface areas, which are partial areas of a third flat or slightly curved surface, and a plurality of second surface areas, which are partial areas of a fourth flat or slightly curved surface, wherein the first sections of the second cutting edge are each present in a first surface area of the second scissor blade and the second sections of the second cutting edge are each present in a second surface area of the second scissor blade.

In medical scissors, as they are described here, the flank surface, the third flat or slightly curved surface, in which the first surface areas of the second scissor blade are located, and the fourth flat or slightly curved surface, in which the second surface areas of the second scissor blade are located, intersect one another especially in the second cutting edge.

The first surface areas of the second scissor blade are especially first partial areas of the beveled surface of the second scissor blade, in which the wedge angle or the cutting angle is relatively small. The second surface areas of the second scissor blade are especially second partial areas of the beveled surface of the second scissor blade, in which the wedge angle or the cutting angle is relatively large.

A medical instrument for microinvasive applications comprises a shaft, the proximal end of which is connected or can be connected mechanically to a handling device, and medical scissors, as they are described here, which are connected or can be connected mechanically to a distal end of the shaft.

The shaft is especially long and thin. The length of the shaft is especially at least 10 times as large as the diameter of the shaft. The shaft may have a linear or curved, rigid or partly or completely flexible configuration.

Embodiments are explained in more detail below on the basis of the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
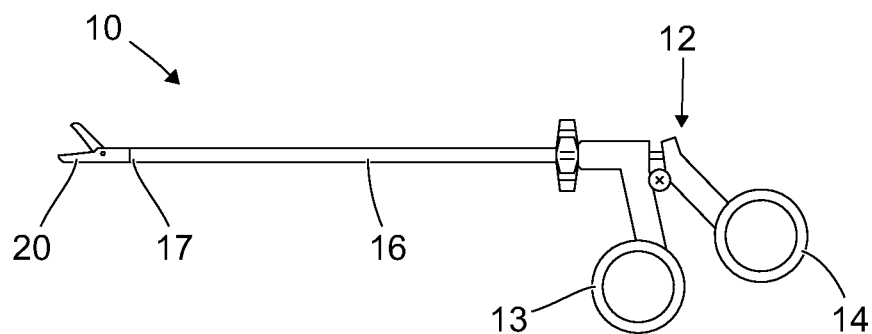
FIG. 1 is a schematic view of a microinvasive medical instrument.

Referring to the drawings, FIG. 1 shows a schematic view of a microinvasive medical instrument 10, the proximal end of which is formed by a handling device 12 with a first grip part 13 and with a second grip part 14. The first grip part 13 of the handling device 12 is mechanically connected to a proximal end of the shaft 16 rigidly, but especially in a non-destructive, detachable manner. A distal end 17 of the shaft 16 is connected mechanically rigidly, but especially in a non-destructive, detachable manner, to the medical scissors 20 as a tool.

Figure 2:
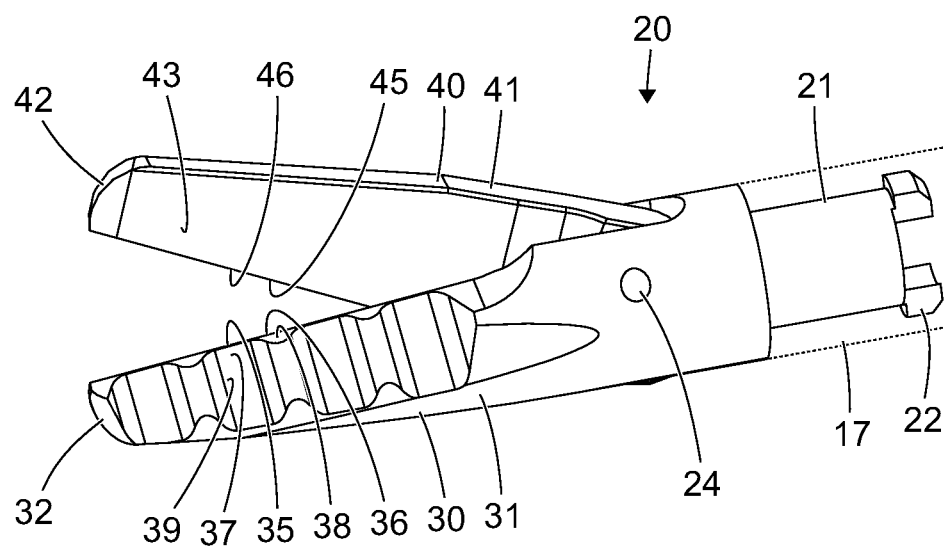
FIG. 2 is a schematic axonometric view of medical scissors.

FIG. 2 shows a schematic and enlarged axonometric view of medical scissors 20. The medical scissors may be part of the medical instrument 10 from FIG. 1 or part of a different medical instrument.

A proximal end 21 of the medical scissors 20 comprises dogs 22 for the mechanical connection in a non-destructive, detachable manner (in the form of a bayonet connection) to a distal end 17, which is only suggested in FIG. 2 in broken contours, of a shaft of a medical instrument, for example, of the medical instrument shown in FIG. 1.

The medical scissors 20 further have a first scissor blade 30, the proximal end 31 of which is rigidly mechanically connected to the proximal end of the medical scissors 20 and thus rigidly though in a non-destructive, detachable manner to the distal end 17 of the shaft of the medical instrument in the example being shown. In the example shown, the first scissor blade 30 even has a monolithic configuration with the proximal end 21 of the medical scissors 20 and the dogs 22.

Between the proximal end 31 and the distal end 32 of the first scissor blade 30, a first cutting edge 35, 36 extends between a flank surface 33, which is facing away from the viewer and is hence not visible in the view in FIG. 2, and a multipart beveled surface 37, 38 which is facing the viewer.

The first cutting edge 35, 36 has alternately first sections 35 and second sections 36. The flat bottoms of wide and flat grooves form first partial areas 37 of the beveled surfaces. These first partial areas 37 form with the flank surface 33 the first sections 35 of the first cutting edge and form with the flank surface 33 a comparatively small wedge angle. The grooves 39 are arranged approximately at right angles to the cutting edge 35, 36.

Oblique end surfaces of webs between the grooves 39 form second partial areas 38 of the beveled surface. These second partial areas 38 form with the flank surface 33 the second sections 36 of the first cutting edge and form with the flank surface 33 a comparatively large wedge angle. The wedge angle between the flank surface 33 and the beveled surface 37, 38 of the first scissor blade 30 is thus markedly smaller at the first sections 35 than at the second sections 36 of the first cutting edge.

In the example shown, the webs between the grooves 39 have markedly rounded cross sections. In the example shown, the first partial areas 37 of the beveled surface are located together in a first plane or in a first slightly curved surface and the second partial areas 38 of the beveled surface are located together in a second plane or in a second slightly curved surface. The first surface and the second surface are slightly curved insofar as their radii of curvature are markedly greater than the length of the first scissor blade.

The medical scissors 20 further comprise a second scissor blade 40 with a proximal end 41, which is pivotably mechanically connected via a joint 24 to the proximal end 21 of the medical scissors and to the first scissor blade 30. The joint 24 defines a pivot axis at right angles to or essentially at right angles to the first cutting edge 35, 36 of the first scissor blade 30. Arranged in the shaft 16 of the medical instrument 10 is a transfer device, in particular a transfer rod, not shown in FIG. 2, which couples the second grip part 14 of the handling device 12 (cf. FIG. 1) with the second, pivotable scissor blade 40 of the medical scissors 20 such that a movement of the second grip part 14 in relation to the first grip part 13 is accompanied by a pivoting movement of the second scissor blade 40 in relation to the first scissor blade 30.

The second scissor blade 40 has a configuration similar to the configuration of the first scissor blade 30. In particular, the second scissor blade 40 has a second cutting edge 45, 46, which extends from the proximal end 41 to the distal end 42 of the second scissor blade 40. The second cutting edge 45, 46 is located between a flank surface 43 facing the viewer in the view shown in FIG. 2 and a multipart beveled surface 47, 48, which is facing away from the view and is hence not visible in the view shown in FIG. 2.

The first cutting edge 35, 36 at the first scissor blade 30 and the second cutting edge 45, 46 at the second scissor blade 40 touch in precisely one point of intersection 50. This is ensured by the joint 24 as guiding device and a slightly prestressing curvature of one of the two scissor blades 30, 40 in the longitudinal direction thereof. This longitudinal curvature cannot be seen in FIG. 2. This longitudinal curvature and the prestressing resulting therefrom are especially selected to be such that the force between the cutting edges 35, 36, 45, 46 is approximately constant, regardless of the location of the point of intersection 50 (cf. FIGS. 2, 3).

Figure 3:
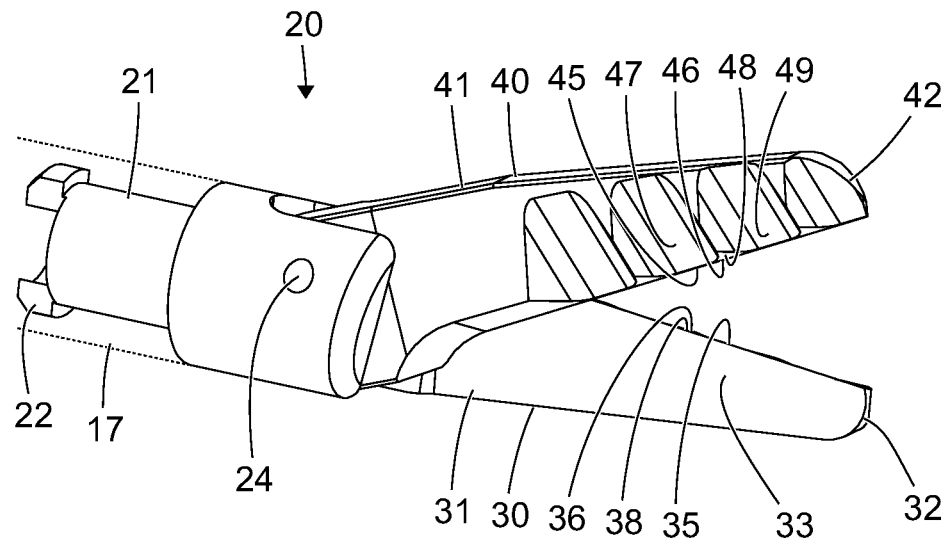
FIG. 3 is another schematic axonometric view of the medical scissors from FIG. 2.

FIG. 3 shows another schematic axonometric view of the medical scissors 20 from FIG. 2. The view in FIG. 3 differs from the view in FIG. 2 by a different, approximately opposite viewing direction. As a result, the flank surface 33 at the first scissor blade 30 and the beveled surfaces 47, 48 of the second scissor blade 40 are facing the viewer and are visible in FIG. 3.

Similarly to the first cutting edge 35, 36 at the first scissor blade 30, the second cutting edge 45, 46 at the second scissor blade 40 also has alternately first sections 45 with a small wedge angle between the flank surface 43 (cf. FIG. 2) and the adjoining first partial area 47 of the beveled surface and second sections 46 with a large wedge angle between the flank surface 43 and the adjoining second partial area 48 of the beveled surface.

Also at the second scissor blade 40, flat bottom surfaces of wide and flat grooves 49 form the first partial areas 47 of the beveled surface with a comparatively small wedge angle to the flank surface. End faces at the ends of webs between the grooves 49 form second partial areas 48 of the beveled surface. These second partial areas 48 of the beveled surface form with the flank surface the second sections 46 of the second cutting edge and form with the flank surface a comparatively large wedge angle. The wedge angle between the flank surface and the beveled surface 45, 46 of the second scissor blade 40 is thus markedly smaller at the first sections 45 than at the second sections 46 of the second cutting edge.

Figure 4:
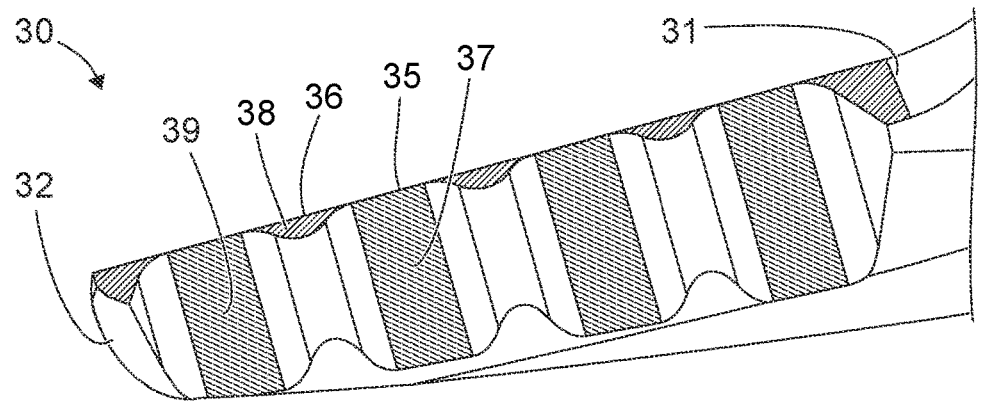
FIG. 4 is another schematic axonometric view of a scissor blade of the medical scissors from FIGS. 2 and 3.

FIG. 4 shows another, enlarged axonometric view of the first scissor blade 30 of the medical scissors from FIGS. 2 and 3. The view in FIG. 4 differs from the view in FIG. 2 by the first partial areas 37 of the beveled surface that adjoin the first sections 35 of the first cutting edge and the partial areas 38 of the beveled surface that adjoin the second sections 36 of the first cutting edge being shaded differently and thus being markedly distinguishable.

In the example shown, all first partial areas 37 of the beveled surface are located in a first slightly curved surface and all second partial areas 38 of the beveled surface are located in a second slightly curved surface. The slight curvature of the first surface and of the second surface cannot be seen in FIG. 4. The curvature results especially from the already mentioned slight curvature of the first scissor blade 30 in its longitudinal direction, which curvature likewise cannot be seen in FIG. 4. The flank surface 33 (cf. FIG. 3), the first surface, in which the first partial areas 37 of the beveled surface are located, and the second surface, in which the second partial areas 38 of the beveled surface are located, may each be curved in one or more directions or be flat, as an alternative.

The first cutting edge 35, 36 of the first scissor blade 30 is the (slightly curved or linear) line of intersection of the flank surface with the first surface, in which the first partial areas 37 of the beveled surface are located, and at the same time, with the second surface, in which the second partial areas 38 of the beveled surface are located.

Figure 5:
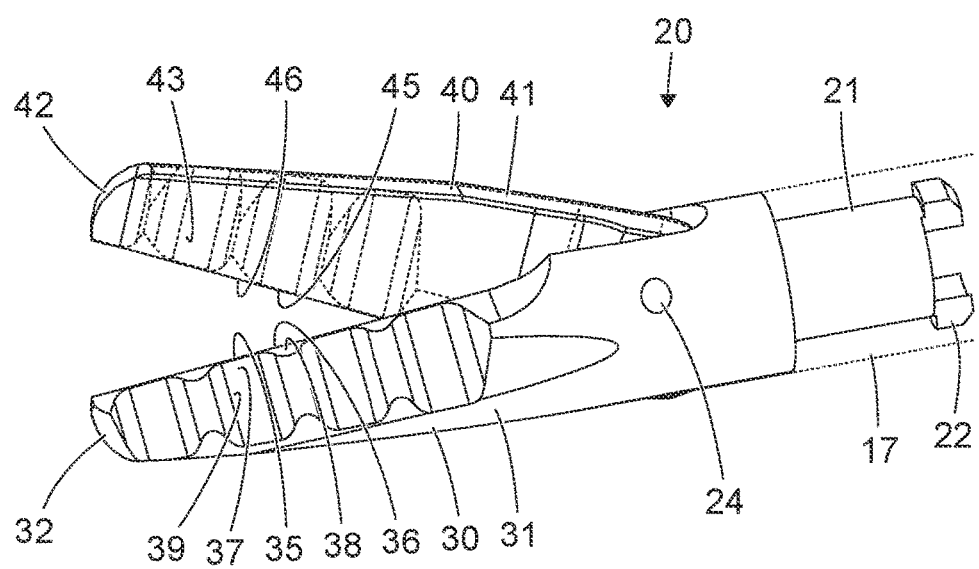
FIG. 5 is another schematic axonometric view of the medical scissors from FIGS. 2 through 4.

FIG. 5 shows another schematic axonometric view of the medical scissors 20 according to FIGS. 2 through 4. The view in FIG. 5 is largely similar to the view in FIG. 2. The view in FIG. 5 differs from the view in FIG. 2 by the structures on the side of the second scissor blade 40 facing away from the viewer being suggested in broken lines.

Figure 6:
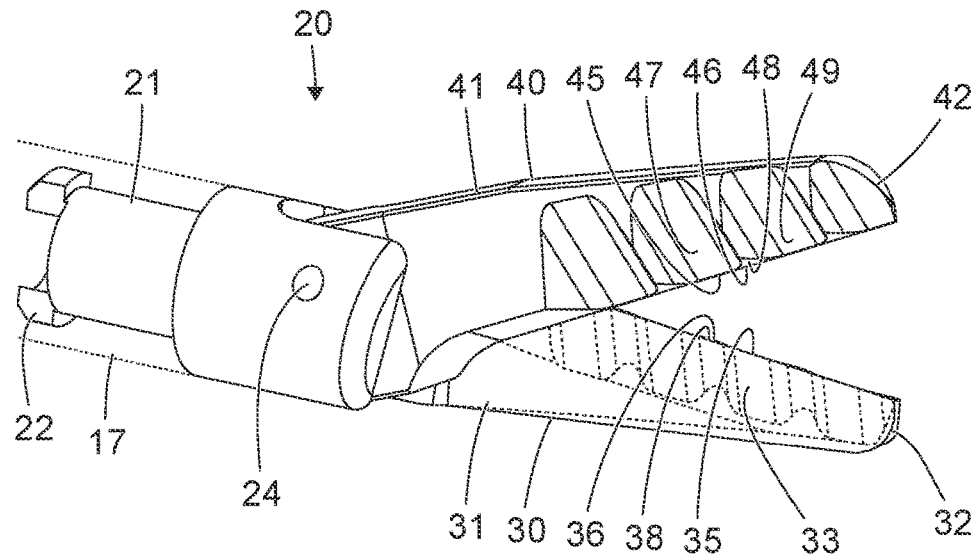
FIG. 6 is another schematic axonometric view of the medical scissors from FIGS. 2 through 5.

FIG. 6 shows another schematic axonometric view of the medical scissors 20 according to FIGS. 2 through 5. The view in FIG. 6 is largely similar to the view in FIG. 3. The view in FIG. 6 differs from the view in FIG. 3 by the structures on the side of the first scissor blade 30 facing away from the viewer being suggested by broken lines.

It can be seen in FIGS. 5 and 6 that the grooves 39 and hence also the first partial areas 37 of the beveled surface at the first scissor blade 30 are arranged offset in relation to the grooves 49 and hence also to the first partial areas 47 of the beveled surface at the second scissor blade 40. A second section 46 of the second cutting edge with a large wedge angle at the second scissor blade 40 is located opposite each first section 35 of the first cutting edge with small wedge angle at the first scissor blade 30. A second section 36 of the first cutting edge with a large wedge angle at the first scissor blade 30 is located opposite each first section 45 of the second cutting edge with a small wedge angle at the second scissor blade 40.

Figure 7:
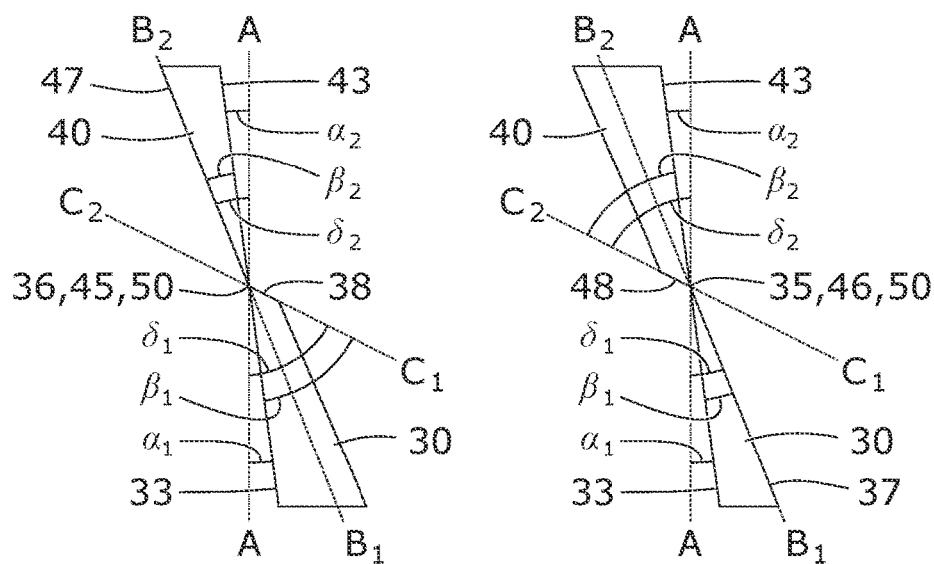
FIG. 7 is schematic views of two sections through the scissor blades of the medical scissors from FIGS. 2 through 6.

FIG. 7 shows a schematic view of two sections through the medical scissors 20 from FIGS. 2 through 6. The sectional planes of FIG. 7 are approximately parallel to the pivot axis defined by the joint 24 (cf. FIGS. 2 through 6) and are approximately at right angles to the cutting edges 35, 36, 45, 46. The sectional plane of FIG. 7 contains the point of intersection 50 of the cutting edges 35, 36, 45, 46.

The cutting plane A is the plane at right angles to the pivot axis defined by the joint 24 (cf. FIGS. 2 through 6), in which the cutting edges 35, 36, 45, 46 are moved in relation to one another.

The flank surface 33 of the first scissor blade 30 forms with the cutting plane or sectional plane A the clearance angle $\alpha_1$. The flank surface 43 of the second scissor blade 43 forms with the cutting plane A the clearance angle $\alpha_2$. Broken lines suggest the positions and orientations of said first surfaces $B_1$, $B_2$, in which the first partial areas 37, 47 of the beveled surfaces of the scissor blades 30, 40 are located, and the positions and orientations of said second surfaces $C_1$, $C_2$, in which the second partial areas 38, 48 of the beveled surfaces of the scissor blades 30, 40 are located.

A situation or configuration of the medical scissors, in which the point of intersection 50 of the first cutting edge at the first scissor blade 30 and of the second cutting edge at the second scissor blade 40 is located between a second section 36 of the first cutting edge with a large value of the wedge angle $\beta_1$ (and hence also of the cutting angle $\delta_1$) and a first section 45 of the second cutting edge with a small value of the wedge angle $\beta_2$ (and hence also of the cutting angle $\delta_2$), similar to the situation shown in FIGS. 2, 3, 5, 6, is shown on the left-hand side in FIG. 7.

A situation or configuration of the medical scissors, in which the point of intersection 50 of the first cutting edge at the first scissor blade 30 and of the second cutting edge at the second scissor blade is located between a first section 35 of the first cutting edge with a small value of the wedge angle $\beta_1$ (and hence also of the cutting angle $\delta_1$) and a second section 46 of the second cutting edge with a large value of the wedge angle $\beta_2$ (and hence also of the cutting angle $\delta_2$) is shown on the right-hand side in FIG. 7.

During the closing the medical scissors, the situations shown on the left-hand side and on the right-hand side in FIG. 7 alternate, so that one of the two wedge angles $\beta_1$, $\beta_2$ has a small value that is usually and only briefly interrupted at the momentary point of intersection 50 of the cutting edges 35, 36, 45, 46.

Figure 8:
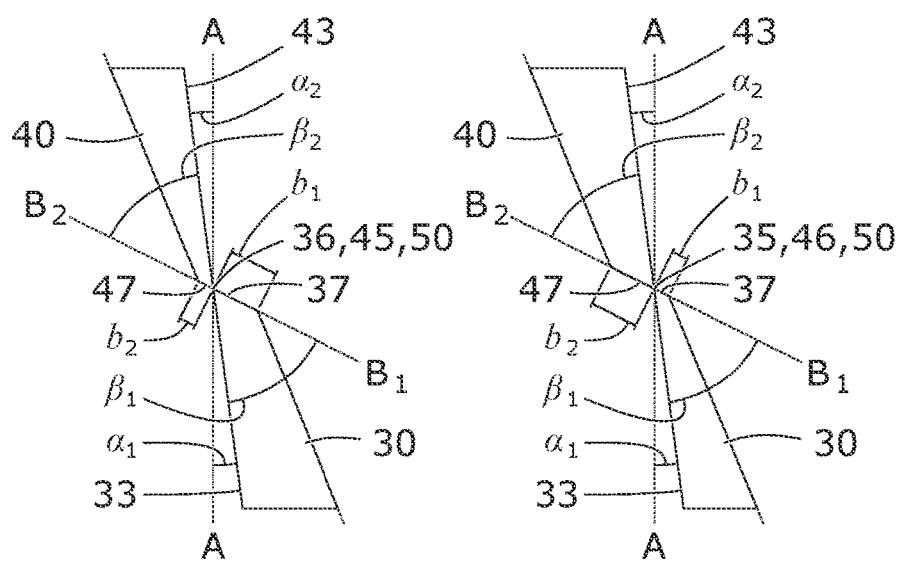
FIG. 8 is schematic views of two sections through another embodiment of the medical scissors.

FIG. 8 shows a schematic view of two sections through an alternative embodiment of the medical scissors, which is similar in some features, properties and functions to the medical scissors shown on the basis of FIGS. 2 through 7. The type of view, especially the sectional planes, corresponds to that of FIG. 7. Below are described especially features, properties and functions of the medical scissors, in which these medical scissors differ from the medical scissors shown on the basis of FIGS. 2 through 7.

The embodiment being shown in FIG. 8 differs from the medical scissors shown on the basis of FIGS. 2 through 7 especially by the wedge angles $\beta_1$, $\beta_2$ along the cutting edges 35, 36, 45, 46 being constant or varying only slowly. Instead of this, the widths $b_1$, $b_2$ of the beveled surfaces 37, 47 vary.

A situation, in which the point of intersection 50 of the cutting edges is in contact with a second section 36 of the first cutting edge with a comparatively large value of the width $b_1$ of the beveled surface 37 of the first scissor blade 30 and with a first section 45 of the second cutting edge with a comparatively small value of the width $B_2$ of the beveled surface 47 at the second scissor blade 40, $b_1 > b_2$, is shown on the left-hand side in FIG. 8.

A situation or configuration of the medical scissors, in which the point of intersection 50 of the cutting edges is in contact with a first section 35 of the first cutting edge with a comparatively small value of the width $B_1$ of the beveled surface 37 of the first scissor blade 30 and with a second section 46 of the second cutting edge with a comparatively large value of the width $B_2$ of the beveled surface 47 at the second scissor blade 40, $b_1 < b_2$, is shown on the right-hand side in FIG. 8.

Figure 9:
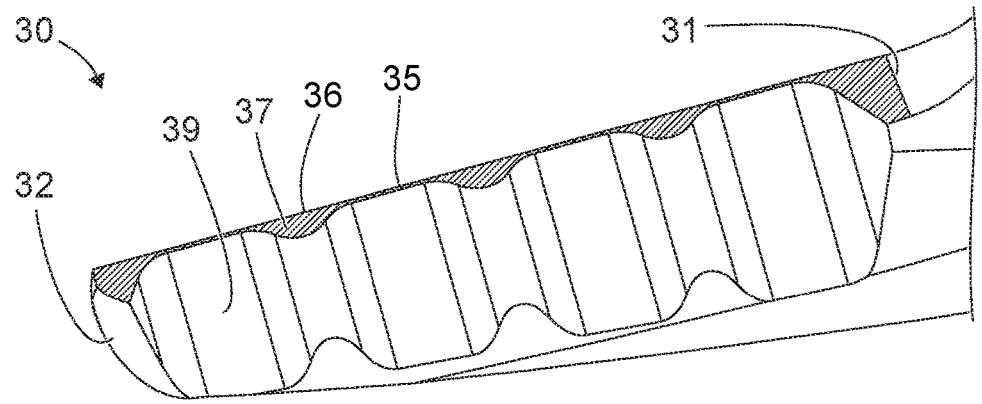
FIG. 9 is a schematic axonometric view of a scissor blade of the embodiment according to FIG. 8.

FIG. 9 shows a schematic axonometric view of the first scissor blade 30 of the medical scissors shown on the basis of FIG. 8. The type of view corresponds to that of FIG. 4.

It can be seen in FIG. 9 that the beveled surface 37 of the first scissor blade 30, which beveled surface 37 is shown in a shaded manner, is continuous, but alternately has very narrow and markedly wider areas. The second scissor blade 40 (cf. FIG. 8) has an especially similar configuration.

The scissor blades 30, 40 may be structured in a manner especially similar to the medical scissors shown on the basis of FIGS. 2 through 7 by producing a plurality of wide and flat grooves 39. Unlike in case of the medical scissors shown on the basis of FIGS. 2 through 7, the grooves 39 do not touch the flank surface 33 (cf. FIG. 8), however, but are arranged at a spaced location from this, so that a groove does not form the beveled surface 37 at any point. Rather, the grooves 39 only modulate the width of the beveled surface 37.

Similarly to the medical scissors shown based on FIGS. 2 through 7, the grooves are also arranged in the medical scissors shown on the basis of FIGS. 8, 9 in the scissor blades 30, 40 offset such that during the closing of the medical scissors the point of intersection 50 of the cutting edges is at any time in contact with at least one section 35, 45 of a cutting edge, in which the width $b_1$, $b_2$ of the beveled surface 37, 47 is smaller than a predefined value.

While specific embodiments of the invention have been shown and described in detail to illustrate the application of the principles of the invention, it will be understood that the invention may be embodied otherwise without departing from such principles.

REFERENCE CHARACTERS

10 Medical instrument for microinvasive applications
12 Handling device of the medical instrument 10
13 First grip part of the handling device 12
14 Second grip part of the handling device 12
16 Shaft of the medical instrument 10
17 Distal end of the shaft 16
20 Medical scissors of the medical instrument 10
21 Proximal end of the medical scissors 20, for the especially detachable, rigid, mechanical connection to the distal end 17 of the shaft 16
22 Dog at the proximal end 21 of the medical scissors, for formation of a bayonet connection between the medical scissors 20 and the distal end 17 of the shaft 16
24 Joint of the medical scissors 20
30 First, especially stationary scissor blade of the medical scissors 20
31 Proximal end of the first scissor blade 30
32 Distal end of the first scissor blade 30
33 Flank surface of the first scissor blade 30
35 First section of a first cutting edge 36 Second section of the first cutting edge
37 Beveled surface of the first scissor blade 30 or first partial area of the beveled surface at the first section 35 of the first cutting edge
38 Second partial area of the beveled surface of the first scissor blade 30 at the second section 36 of the first cutting edge
39 Groove on the side of the first scissor blade 30 facing away from the flank surface 33
40 Second, especially pivotable scissor blade of the medical scissors 20
41 Proximal end of the second scissor blade 40
42 Distal end of the second scissor blade 40
43 Flank surface of the second scissor blade 40
45 First section of a second cutting edge
46 Second section of the second cutting edge
47 Beveled surface of the second scissor blade 40 or first partial area of the beveled surface at the first section 45 of the second cutting edge
48 Second partial area of the beveled surface of the second scissor blade 40 at the second section 46 of the second cutting edge
49 Groove on the side of the second scissor blade 40 facing away from the flank surface 43
50 Point of intersection of the first cutting edge 35, 36 and of the second cutting edge 45, 46
A Cutting plane or cutting surface
$B_1$ First flat or slightly curved surface, in which the first partial areas 37 of the beveled surface of the first scissor blade 30 are located
$B_2$ First flat or slightly curved surface, in which the first partial areas 37 of the beveled surface of the first scissor blade 30 are located
$C_1$ Second flat or slightly curved surface, in which the second partial areas 38 of the beveled surface of the first scissor blade 30 are located
$C_2$ Second flat or slightly curved surface, in which the second partial areas 48 of the beveled surface of the second scissor blade 40 are located
$\alpha_1$ Clearance angle of the flank surface 33 at the first scissor blade 30
$\beta_1$ Wedge angle between the flank surface 33 and the beveled surface at the first scissor blade 30
$\delta_1$ Cutting angle at the first scissor blade 30, $\delta_1=\alpha_1+\beta_1$
$b_1$ Width of the beveled surface 37, 38 of the first scissor blade
$\alpha_2$ Clearance angle of the flank surface 43 at the second scissor blade 40
$\beta_2$ Wedge angle between the flank surface 43 and the beveled surface at the second scissor blade 40
$\delta_2$ Cutting angle at the second scissor blade 40, $\delta_2=\alpha_2+\beta_2$
$b_2$ Width of the beveled surface 47, 48 of the second scissor blade

What is claimed is:

1. Medical scissors for microinvasive applications, the medical scissors comprising:
a first scissor blade with a first cutting edge between a first blade flank surface and a first blade beveled surface;
a second scissor blade with a second cutting edge between a second blade flank surface and a second blade beveled surface, the second scissor blade being movable in relation to the first scissor blade;
a guiding device for the mechanical guiding of the second scissor blade in relation to the first scissor blade such that the second cutting edge touches the first cutting edge at any time at a point of intersection, wherein:
the guiding device is rigidly connected to a shaft of a microinvasive instrument or is connectable to a shaft of a microinvasive instrument;
the first cutting edge is configured based on a first parameter which increases several times and decreases several times along the first cutting edge;
the second cutting edge is configured based on a second parameter which increases several times and decreases several times along the second cutting edge;
the first parameter is a wedge angle between the first blade flank sur and the first blade beveled surface, or a first cutting edge cutting angle, or a width of the first blade beveled surface;
the second parameter is a wedge angle between the second blade flank surface and the second blade beveled surface or a second cutting edge cutting angle or a width of the second blade beveled surface; and
the guiding device and the first and second cutting edges are configured such that the first and second cutting edges touch each other at any time at only one intersection point.

2. Medical scissors in accordance with claim 1, wherein:
the first cutting edge has alternately first edge first sections, in which the first parameter is not greater than a first predefined value, and first edge second sections, in which the first parameter is not smaller than a second predefined value, which second predefined value is greater than the first predefined value;
the second cutting edge has alternately second edge first sections, in which the second parameter is not greater than a third predefined value, and second edge second sections, in which the second parameter is not smaller than a fourth predefined value, which fourth predefined value is greater than the third predefined value; and
each of the first edge second sections is located opposite one of the second edge first sections and each of the second edge second sections is located opposite one of the first edge first sections.

3. Medical scissors in accordance with claim 2, wherein the first edge first sections and the first edge second sections and the second edge first sections and the second edge second sections are arranged such that the point of intersection is located at any time at least either at one of the first edge first sections or one of the second edge first sections during the closing of the medical scissors.

4. Medical scissors in accordance with claim 2, wherein the first edge first sections and the first edge second sections and the second edge first sections and the second edge second sections are arranged such that, during closing of the medical scissors areas with the point of intersection located neither at one of the first edge first sections nor at one of the second edge first sections are not larger than respective, directly adjacent areas with the point of intersection located at one of the first edge first sections or one of the second edge first sections.

5. Medical scissors in accordance with claim 2, wherein at least either:
the first parameter is identical to the first predefined value in each first edge first section; or
the second parameter is identical to the third predefined value in each second edge second section.

6. Medical scissors in accordance with claim 5, wherein the first predefined value and the third predefined value are identical.

7. Medical scissors in accordance with claim 2, wherein:
a side of the first scissor blade facing away from the first flank surface has grooves oriented essentially at right angles to the first cutting edge;
the first edge first sections are each present in a respective one of the grooves; and
the first edge second sections are present between adjacent grooves.

8. Medical scissors in accordance with the claim 7, wherein a cross section of at least one of the grooves has a linear edge section that is parallel to the first cutting edge.

9. Medical scissors in accordance with claim 7, wherein a web which remains between adjacent grooves has a rounded cross section.

10. Medical scissors in accordance with claim 2, wherein:
a side of the second scissor blade facing away from the second flank surface has grooves that are oriented essentially at right angles to the second cutting edge;
the second edge first sections are each present in a respective one of the grooves; and
the second edge second sections are present between adjacent grooves.

11. Medical scissors in accordance with claim 1, wherein:
a side of the first scissor blade facing away from the first flank surface has a plurality of first surface areas, which are partial areas of a first flat or slightly curved surface, and a plurality of second surface areas, which are partial areas of a second flat or slightly curved surface;
each of the first sections of the first cutting edge is present in a first surface area of the first scissor blade; and
each of the second sections of the first cutting edge is present in a second surface area of the first scissor blade.

12. Medical scissors in accordance with claim 11, wherein the first flat or slightly curved surface, located in the first surface areas, and the second flat or slightly curved surface, located in the second surface areas, intersect one another in the first cutting edge.

13. A medical instrument for microinvasive applications, the medical instrument comprising:
a shaft with a distal end and with a proximal end connected to or connectable to a handling device; and
medical scissors connected or connectable mechanically to the distal end of the shaft, the medical scissors comprising:
a first scissor blade with a first cutting edge between a first blade flank surface and a first blade beveled surface;
a second scissor blade with a second cutting edge between a second blade flank surface and a second blade beveled surface, the second scissor blade being movable in relation to the first scissor blade;
a guiding device for the mechanical guiding of the second scissor blade in relation to the first scissor blade such that the second cutting edge touches the first cutting edge at any time at a point of intersection, wherein:
the guiding device is rigidly connected to the shaft or is connectable to the shaft;
the first cutting edge is configured based on a first parameter which increases several times and decreases several times along the first cutting edge;
the second cutting edge is configured based on a second parameter which increases several times and decreases several times along the second cutting edge;
the first parameter is a wedge angle between the first blade flank surface and the first blade beveled surface or a first cutting edge cutting angle or a width of the first blade beveled surface;
the second parameter is a wedge angle between the second blade flank surface and the second blade beveled surface or a second cutting edge cutting angle or a width of the second blade beveled surface; and
the guiding device and the first and second cutting edges are configured such that the first and second cutting edges touch each other at any time at only one intersection point.

14. A medical instrument in accordance with claim 13, wherein:
the first cutting edge has alternately first edge first sections, in which the first parameter is not greater than a first predefined value, and first edge second sections, in which the first parameter is not smaller than a second predefined value, which second predefined value is greater than the first predefined value;
the second cutting edge has alternately second edge first sections, in which the second parameter is not greater than a third predefined value, and second edge second sections, in which the second parameter is not smaller than a fourth predefined value, which fourth predefined value is greater than the third predefined value; and
each of the first edge second sections is located opposite one of the second edge first sections and each of the second edge second sections is located opposite one of the first edge first sections.

15. A medical instrument in accordance with claim 14, wherein the first edge first sections and the first edge second sections and the second edge first sections and the second edge second sections are arranged such that the point of intersection is located at any time at least either at one of the first edge first sections or one of the second edge first sections during the closing of the medical scissors.

16. A medical instrument in accordance with claim 14, wherein the first edge first sections and the first edge second sections and the second edge first sections and the second edge second sections are arranged such that during closing of the medical scissors areas with the point of intersection located neither at one of the first edge first sections nor at one of the second edge first sections, are not larger than respective, directly adjacent areas with the point of intersection located at one of the first edge first sections or one of the second edge first sections.

17. A medical instrument in accordance with claim 14, wherein at least either
the first parameter is identical to the first predefined value in each first edge first section; or
the second parameter is identical to the third predefined value in each second edge second section.

18. A medical instrument in accordance with claim 14, wherein
a side of the first scissor blade facing away from the first flank surface has grooves oriented essentially at right angles to the first cutting edge;
the first edge first sections are each present in a respective one of the grooves; and
the first edge second sections are present between adjacent grooves.

19. A medical instrument in accordance with claim 14, wherein:

a side of the second scissor blade facing away from the second flank surface has grooves that are oriented essentially at right angles to the second cutting edge;

the second edge first sections are each present in a respective one of the grooves; and the second edge second sections are present between adjacent grooves.

\* \* \* \* \*